United States Patent [19]

McGraw, III

[11] Patent Number: 5,215,884

[45] Date of Patent: Jun. 1, 1993

[54] SEX-SPECIFIC DNA PROBES

[75] Inventor: Royal A. McGraw, III, Athens, Ga.

[73] Assignee: University of Georgia Research Foundation, Inc., Athens, Ga.

[21] Appl. No.: 728,840

[22] Filed: Jul. 9, 1991

Related U.S. Application Data

[63] Continuation of Ser. No. 146,320, Jan. 21, 1988, abandoned.

[51] Int. Cl.[5] .................. C12Q 1/68; C07H 17/00
[52] U.S. Cl. .................................. 435/6; 435/172.1; 435/320.1; 435/91; 436/501; 436/811; 536/27; 935/9; 935/19; 935/29; 935/78; 935/86; 935/88
[58] Field of Search ............. 435/6, 172.1, 320, 1, 435/91; 436/501, 811; 536/27; 935/9, 19, 29, 78, 86, 88

[56] References Cited

U.S. PATENT DOCUMENTS 4,769,319 9/1988 Ellis et al. ....................... 435/6

FOREIGN PATENT DOCUMENTS

PCT/AU87/-
 00254 3/1988 Australia .

OTHER PUBLICATIONS

Kodama et al. (1987) Chromosoma, vol. 96, pp. 18–25.
Tone et al., (1982) Chromosoma, vol. 86, pp. 551–569.
Bostock, et al., Nature 272:324–328 (1978).
Cooke, Nature 262:182–186 (1976).
Cooke, Chromosoma 87, 491–502 (1982).
Epplen, et al., Proc. Natl. Acad. Sci., USA, 79:3798–3802 (1982).
Leonard, et al., Theriogenology 27:248 (1987).
Phillips, et al., Nature 297:241–243 (1982).
McGraw, et al., Nucleic Acids Research, vol 16, No. 21, p. 10389 (1988).
Akamatsu, et al., Nucleic Acids Research, vol. 17, No. 23, p. 10120 (1989).
Mileham, et al., Nucleic Acids Research, vol. 16, No. 24, p. 11842 (1988).

Primary Examiner—Amelia Burgess Yarbrough
Assistant Examiner—Ardin H. Marschel
Attorney, Agent, or Firm—Kilpatrick & Cody

[57] ABSTRACT

The present invention are nucleic acid probes which are highly selective for DNA specific to one sex of a livestock species, particularly pigs and chickens, and methods for their isolation, characterization, and utilization. These probes can be applied in a variety of methods for assaying the ratio of male to female mammalian sperm in an isolated fraction or the sex of an egg, as well as for determining the sex of an embryo in the early stages of development.

Genomic DNA from whole blood taken from a male and a female animal was digested with various restriction enzymes and the products compared on agarose gels. A band of approximately 4 kilobases in a EcoR1 digest of male pig DNA was absent in female pig DNA. In the chickens, a band of approximately 600 bases and a band of approximately 1200 bases were present in a XhoI digest of female DNA which was not present in the male DNA. The sex-specific DNA was then ligated into a vector and transformed into E. coli. The resulting vector DNA was shown by restriction analysis to contain the expected insert. The male pig-specific plasmid was deposited with the American Type Culture Collection, Rockville, Md. on Jan. 21, 1988 and assigned ATCC number 40417. The insert fragment was isolated, labelled, and shown to hybridize specifically with male pig DNA. The female chicken-specific clone was deposited with the ATCC on Jan. 21, 1988 and assigned ATCC number 40418. Probes made from the isolated insert were shown to specifically hybridize with female chicken DNA.

The cloned fragment and subfragments thereof were recloned into the sequencing vector M13 for sequencing using standard techniques.

8 Claims, 3 Drawing Sheets

SEX-SPECIFIC DNA PROBES

This is a continuation of copending application Ser. No. 07/146,320 filed on Jan. 21, 1988, now abandoned.

BACKGROUND OF THE INVENTION

Sex determination in mammals is well understood at this time. In essentially all mammalian species, females have two XX chromosomes and males have one X and one Y chromosome. The important role of the Y chromosome as a determiner of male characteristics is apparent in view of the rare individuals with numerical abnormalities of the sex chromosomes. Individuals with two XX chromosomes and one y, Klinefelter's syndrome, are phenotypically male, while individuals with a single X and no Y, Turner's syndrome, are female. Similarly, XO mice and pigs are female, while XXY mice and cats are male.

The sex chromosomes in birds are the reverse of mammals. Male birds are homogametic, having two Z chromosomes, while females are heterogametic, having one Z and one W chromosome. As a result, the sex of the offspring is determined by the genetic content of the egg rather than the sperm.

Individual mammalian spermatozoa, being haploid, contain either a single X or a single Y chromosome, while the haploid eggs all contain single X chromosomes. The sperm therefore determines the sex of the conceptus. A single ejaculate contains many millions of sperm cells, with male and female determining types usually present in roughly equal amounts.

There are tremendous economic incentives in the livestock industry to develop a means for providing sperm for artificial insemination for which the ratio of one sex to the other sex is known. In the dairy industry, there is a greater demand for female offspring. In the pig industry in the United States, there is more preference for female is for pork production. Fractionations of semen by sex have been attempted based on a variety of physical, biochemical, and immunological methods. For the most part, successes have been marginal. A key part of any chemical or biochemical separation procedure is the assay of fractions. The assays now available, such as cytological examination of chromosomes or direct examination of live births, tend to be prohibitively tedious, slow, or expensive.

The best studied mammalian chromosomes are those of man, yet only a few genes thus far have been mapped on the human Y chromosome, possibly due to its small size. To the extent that the human gene map reflects the situation in farm animals, there are some Y-linked genes involved in fertility and growth that might be important in livestock production.

A prominent feature of the human Y chromosome DNA is a highly repeated sequence not found in females, as described by Bostock, et al, *Nature* 272,324-328 (1978) and Cooke et al, *Chromosoma* 87,491-502 (1982). Due to its repetitive nature, this material can be visualized directly as a 3.4 kilobase ethidium-staining band by agarose el electrophoresis of male DNA after digestion with the restriction enzyme HaeIII. This sequence occurs as a tandem array of several thousand copies, possibly representing as much as 30% of the human Y chromosome.

The existence of comparable Y-specific repeats in economically important livestock animals is not well-documented. See Epplen et al, *Proc.Natl.Acad.Sci. USA* 79,3798-3802 (1982); Phillips et al, *Nature,* 297,241-243 (1982); Ohno et al, *Sexual Differentiation; Basic and Clinical Aspects,* M. Serio et al. ed. (Raven Press, N.Y. 1984). Although there is cytological evidence indicating that the Y chromosome has been well-conserved in evolution among the various mammalian species, reported by Matthey and Vorontsov, *Cytotaxonomy and Vertebrate Evolution,* Chiarelli and Capanna, eds.,5-31-553 (Academic Press, London 1973), Research by Leonard et al, *Therioenology* 27,248 (Proc.Ann.Conf.Internat.Embryo Transfer Soc., Dublin, Ireland, Jan. 25-27, 1987) indicates that the human male specific HaeIII DNA fragment is not suitable as a sex-specific probe in cattle.

Leonard et al describe the use of a Y chromosome-specific DNA probe in the sexing of bovine embryos. Embryos were collected at 7-8 days of gestation from superovulated heifers. Biopsies consisting of 10-20 trophoblastic cells were assayed by in situ hybridization with a biotinylated Y-specific DNA probe. Male embryos were identified by their positive hybridization signals, as detected by an immunocytochemical procedure. This bovine sex-specific sequence consists of a 49 nucleotide tandem repetition which is cleavable by the restriction enzyme Sau3A. The same sequence is detectable as a seven kilobase EcoRI fragment in genomic Southern blots.

It is therefore an object of the present invention to provide a method for identifying sex-specific DNA's in livestock animals, especially pigs and chickens.

It is another object of the present invention to clone and characterize sex-specific DNA sequences.

It is a further object of the present invention to provide sex-specific DNA probes.

It is a still further object to provide methods and probes to assay the sex ratios in semen fractions or unfertilized eggs.

It is another object of the present invention to provide a method and probes to determine the sex of embryos.

SUMMARY OF THE INVENTION

The present invention are nucleic acid probes which are highly selective for DNA specific to one sex of a livestock species and methods for their isolation, characterization, and utilization. These probes can be applied in a variety of methods for assaying the ratio of male to female mammalian sperm in an isolated fraction or the sex of an egg, as well as for determining the sex of an embryo in the early stages of development.

Genomic DNA from whole blood taken from a male and a female animal (pigs and chickens) was digested with various restriction enzymes and the products compared on agarose gels. A band of approximately 4 kilobases in a EcoR1 digest of the male pig DNA was absent in female pig DNA. In the chickens, a band of 600 bases and a band of 1200 bases were present in a XhoI digest of the female DNA which was not present in the male DNA. Larger, preparative digests were done and the sex-specific band eluted from a gel slice and purified further. A portion of the eluted material was labelled with $P^{32}$ by the random-primer method. This probe was tested in a Southern blot of male and female genomic DNAs digested with the appropriate restriction enzyme. Resulting autoradiograms confirmed the sex-specificity of the probe.

The male-specific pig DNA was then ligated into the EcoRI site of the plasmid vector pUC8 and transformed into *E. coli* strain JM83. A positive colony was picked, grown in large culture, and the plasmid DNA purified. The resulting plasmid DNA was shown by restriction analysis to contain the expected 4 kb EcoRI insert. This plasmid was deposited with the American Type Culture Collection, Rockville, Md. on Jan. 21, 1988 and assigned ATCC number 40417. The insert fragment was isolated, labelled, and shown to hybridize specifically with male pig DNA.

The cloned fragment and subfragments thereof were re-cloned into the sequencing vector M13mp9 for sequencing using standard techniques.

The same techniques were applied to the sex-specific chicken DNA and clones obtained. A clone of the female-specific chicken DNA in pUC9 was deposited with the ATCC on Jan. 21, 1988 and assigned ATCC number 40418. Probes made from the isolated insert were shown to specifically hybridize with female chicken DNA.

DETAILED DESCRIPTION OF THE INVENTION

Figure 1B:
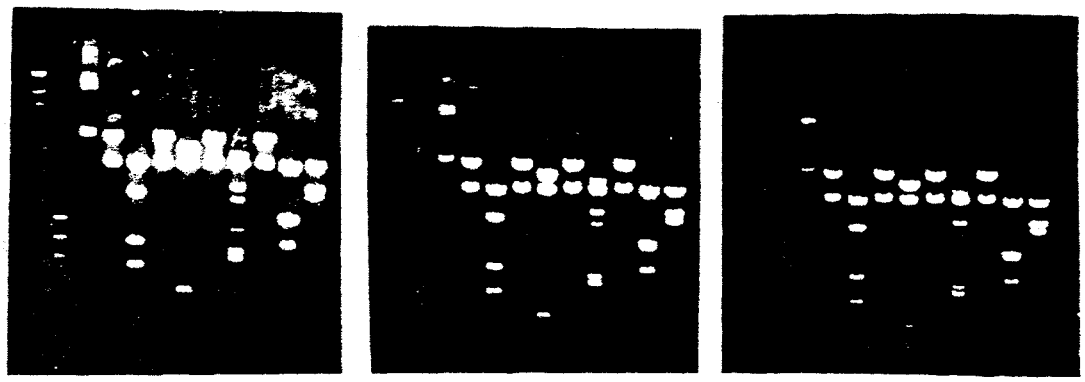
FIG. 1 are gels demonstrating the results of single (1A), double (1B), and triple (1C) restriction enzyme digestion of the plasmid containing the pig sex-specific DNA sequence.

The DNA sequence of the present invention is especially valuable in the identification and characterization of sex-specific DNAs in economically important livestock species, in particular, the pig and the chicken. The sequence can be used to develop sex-specific DNA probes. Specific applications include assays for sex fractionated semen, unfertilized eggs, and sex identification in early embryos. In most livestock species, one sex has significantly greater market value than the other. In the United States, there is a preference for female pigs for pork production. With chickens raised for eg production, there is a much greater demand for female chicks.

The probes of the resent invention can be utilized in combination with standard molecular genetic procedures including restriction enzyme digestions, electrophoretic separations, propagations of recombinant DNA in plasmid and phage vectors, sequence analysis, and hybridizations using labeled probes to produce better control over sex ratios in livestock production. Other techniques which are known to those skilled in the art, including field inversion electrophoresis for better separations of large DNA molecules, amplifications of target sequences by polymerase chain reaction, and chemical synthesis of sex-specific DNA probes, can be employed to optimize utilization of the sex-specific sequence. The probes can also be used in the development of new assays using immunochemical or biochemical technology.

The following methods are useful for manipulation of DNA as required to isolate and utilize sex-specific DNA according to the present invention Many of these methods are described in *Molecular Cloning: A Laboratory Manual*, T. Maniatis, et al (Cold Spring Harbor Press, N.Y. 1982). Blood and semen samples are obtained using standard methods.

For the identification of sex-specific DNA's, somatic DNA is purified from whole blood or tissue specimens from male and female animals by lysis with detergent, digestion with proteinase, repeated extractions with phenol and chloroform, and ethanol precipitation. Several milligrams of high molecular weight DNA can be obtained from 50 milliliters of blood or a few grams of tissue. 5-10 micrograms aliquots of the purified DNA are digested with various restriction enzymes and the resulting fragments are separated according to size by electrophoresis in 0.7% agarose gels. The gels are stained with ethidium bromide and viewed in UV light. Direct comparison of male and female DNA's by this method reveals sex-specific bands in some species.

Sex-specific DNAs can be cloned and characterized by excising bands from the gels followed by re-purification by NACS column (Gibco-BRL) chromatography. In some cases it may be helpful to employ field inversion electrophoresis, as described by Carle et al., *Science*, 232, 65–68 (1986), to more effectively resolve the desired bands from co-migrating genomic DNA.

Aliquots of the gel-purified DNA can be labelled directly using the method of Feinberg and Vogelstein, *Analytical Biochemistry*, 132,6–9 (1983) and used to probe blots, as taught by Southern, *J.Mol.Biol.* 98,503(1975); Parnes et al., *Proc.Natl.Acad.Sci.USA*, 78,2253(1981), of male and female genomic DNA in order to assess their sex-specificity. Additional aliquots can be ligated directly into vectors such as M13 phage for propagation in bacteria.

The reagents utilized in these methods are commercially available from a number of companies including New England Nuclear, Boston, Mass.; New England Biolabs, Inc., Beverly, Mass.; Pharmacia LKB Biotechnology Inc., Piscataway, N.J.; Promea Corp., Madison, Wis.; Sigma Chemical Co., St. Louis, Mo.; Bethesda Research Laboratories (BRL) and Boehringer Mannheim Biochemicals, Indianapolis, Ind.

The nucleic acid probes are highly selective for DNA from a single sex and methods for their isolation, characterization, and utilization and can be applied in a variety of methods for assaying the ratio of male to female sperm in an isolated fraction (in the case of the pig probe) or the sex of an unfertilized egg (in the case of the chicken probe) and for determining the sex of an embryo in the early stages of development.

Sex-specific clones are radioactively labeled and hybridized to male and female genomic DNA. Clones showing a clear pattern of sex-specific hybridization can be sequenced in their entirety. Nucleotide sequences can be determined by the M13 dideoxy chain-terminating method (Sanger et al *J. Mol.Biol.*, 94,441 (1977) with improvements by Messin, et al, *Nucleic Acids Res.* 9,309 (1981). In the event that cloned sequences are too long to be sequenced completely by priming from the universal site in M13 (>500 base pairs), additional clone-specific primers can be synthesized chemically to allow extension of the sequencing further into the cloned region, using a method such as that described by Sanchez-Pescador and Urdea, *DNA.* 3, 339–343 (1984).

Depending on the character of the sex-specific sequences, it may be desirable to chemically synthesize probes for further experimentation, rather than continuing to use cloned material. For example, this may be the case with the probes of the present invention where the sex-specific sequences consist of multiple tandem repeats of a relatively short (<100 base pairs) sequence. Synthesis can be done manually by a variation of the method of Frank et al., *Nucleic Acids Res.* 11,4365–4377 (1983) of the phosphotriester (Efimov et al., *Nucleic Acids Res.* 14,6525–6540 (1986)) and/or phosphoramidite (Beaucae and Caruthers, *Tetrahedron Lett,* 22,1859–1962 (1981) chemistries.

To determine sex ratio in semen, DNA is isolated from semen by a method such as that of Borenfreund, *Nature,* 101,1375–1376 (1961). Using radioactively labeled male-specific hybridization probes, it is possible to measure the proportion of male-specific DNA present in semen specimens. Measured values are compared with those obtained from a standard curve prepared by mixing male and female somatic DNAs in varying proportions. A gualitative assay can be done by spotting test DNA onto nitrocellulose filters, hybridizing to the filters, and then gauging the extent of hybridization by autobiography.

A more precise determination can be made by solution hybridization in which the radioactive probe is mixed with test DNA in solution. Both probe and test DNA are added in single-stranded form. After a suitable hybridization period, determined by the formation of double-stranded DNA, the extent of hybridization is measured by digesting any remaining single strands With a single-strand-specific nuclease such as nuclease S1, collecting the S1-resistant DNA on filters, and counting the filters in a scintillation counter.

The sex of embryos can be determined in a similar manner, using DNA extracted from a biopsy or sloughed tissue. Synthetic oligonucleotides can be used in place of or in addition to the cloned DNA. Two methods exist at this time for sampling the fetal cells. Since trophoblast tissue is of embryonic origin, the presence of Y-specific DNA sequences in trophoblast biopsies is indicative of the presence of a male fetus. Purification and analysis of the DNA from such specimens should be straightforward. In the second method, DNA is isolated from the fertilized egg.

In the case of poultry, DNA must be isolated DNA from eggs (both fertilized and unfertilized), since sex in poultry is determined by the female gamete.

The present invention is further described by the following non-limiting examples.

PIG

Genomic DNA from whole blood taken from a male and a female pig was digested with various restriction enzymes and the products compared on agarose gels. A band of approximately 4 kilobases in the EcoR1 digest of the male DNA was absent in female DNA. Larger, preparative digests were subsequently made and the male-specific band eluted from a gel slice and purified further. A portion of the eluted material was labelled with $P^{32}$ by the random-primer method. This probe was tested in a Southern blot of male and female genomic DNAs digested with EcoR1. Resulting autoradiograms confirmed the sex-specificity of the probe.

This sex-specific DNA was then ligated into the EcoR1 site of the plasmid vector pUC8 and transformed into *E. coli* strain JM83. Resulting colonies were screened for the presence of the insert by hybridization with a probe similar to the one used in the Southern blot. A positive colony was picked, grown in large culture, and plasmid DNA was purified by CsCl gradient.

The resulting plasmid DNA was shown by restriction analysis to contain the expected 4 kb EcoR1 insert. This plasmid was deposited with the American Type Culture Collection, Rockville, Md. on Jan. 21, 1988 and assigned ATCC number 40417. The insert fragment was isolated, labelled, and shown to hybridize specifically with male pig DNA both in dot blots and in Southern blots. Prolonged exposure of the Southern blots indicated that sequences hybridizing to the cloned probe were present in female DNA, but at a very much reduced level (less than 300-fold).

EXAMPLE OF THE ISOLATION OF SEX-SPECIFIC DNA

DNA was extracted from whole pig blood (40 ml) by adding 1.0 M Tris Tm-HCl (pH 8.0), 0.5 M EDTA, and 10% SDS to a final concentration of 0.1M Tris, 0.05M EDTA, and 1% SDS, followed 30 min later with 10 mg Sigma proteinase K. DNA was then purified by repeated extraction with buffer-saturated phenol (research grade phenol neutralized and saturated with 1.0M Tris Tm-HCl base). DNA, remaining in the aqueous layer, is recovered by precipitation with 0.1M sodium acetate and 2.5 volumes ethanol. The precipitated DNA is dissolved in 10 mM Tris Tm-HCl, 0.1 mM EDTA (TE).

The DNA was digested with EcoRI, HindIII, BamHI, PstI, BlII and PvuII and electrophoresed on a 0.7% agarose el. Band patterns from male and female pigs were then compared and the DNA from the band present only in the male pig isolated from the gel.

EXAMPLE OF THE PREPARATION OF A PROBE FOR SEX-SPECIFIC DNA 5 microliters DNA isolated from the sex-specific band, 2 microliters hexamers, 3 microliters TE were heated to 95° C. for 2 min then cooled on ice. 10 microliters of a 2.5 x TE-deoxynucleoside triphosphates mix (dGTP, dCTP, dTTP) were then added, followed by addition of 1 microliter bovine serum albumin, 2 microliters $\alpha P^{32}$-labelled dATP, and 1 microliter of Klenow fragment (large fragment of *E. coli* DNA polymerase I, BRL). The mixture was incubated at room temperature 1 h, then the labelled DNA used as a probe in a Southern blot of male and female genomic DNAs digested with EcoRI. The resulting autoradiogram demonstrated that the probe contains sex-specific DNA.

EXAMPLE OF THE CONSTRUCTION OF A VECTOR CONTAINING THE SEX-SPECIFIC DNA

The sex-specific DNA eluted from the gel in the first example was ligated into the EcoR1 site of plasmid pUC8 (available from commercial sources such as Promea Corp) and transformed into *E. coli* strain JM83.

The vector DNA was prepared as follows. pUC8 was linearized with EcoR1 according to the manufacturer's instructions. 2 microliters calf alkaline phosphatase (C. F. Boehriner & Soehne GmbH, Mannheim. W. Germany) was added and the mixture incubated at 37° C. one h. The vector DNA was then purified by repeated phenol extraction and ethanol precipitation, then redissolved in TE.

The sex-specific DNA was ligated as follows: 3 microliters pUC8/EcoR1, 3 microliters 100 mM MgCl2, 3 microliters 100 mM Dithiothreitol, 3 microliters 10 mM rATP, 3 microliters 1 M Tris Tm-HCl, 6 microliters sex specific pig DNA, 7.5 microliters TE, and 1.5 microliters T4 ligase were combined. The reaction was incubated overnight at 15° C. The mixture was then diluted to 100 microliters with TE. 20 microliters mixture was added to 200 microliters competent *E. coli* cells (prepared using standard procedures), allowed to transform 45 min on ice, heat shocked at 42° C. for 1 min, cooled, 780 microliters L broth (available from Difco) added and the cells cultured 30 min at 37° C. 100 microliters of the cells were then spread on AXI (ampicillin, Xgal, IPTG) plates. Approximately 31 recombinant colonies were recovered.

Four plasmids from the recombinant colonies were picked and grown in 1 ml culture, then transferred RAM to 500 ml cultures for overnight growth in media containing 100 microgram Amp/ml media. The cells were then extracted in a CsCl gradient and samples dialyzed after isopropanol treatment, according to the method of Maniatis, et al, page 90. The presence of the DNA insert in the plasmid was confirmed by gel electrophoresis following digestion with EcoRI.

Figure 1A:
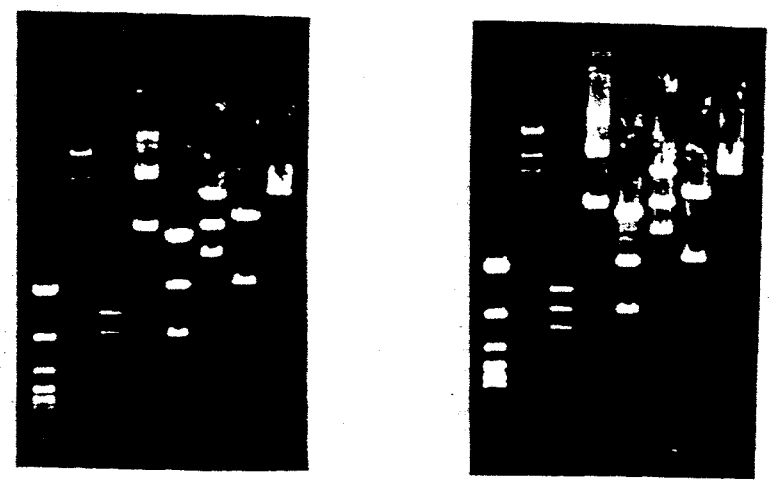
Figure 1C:
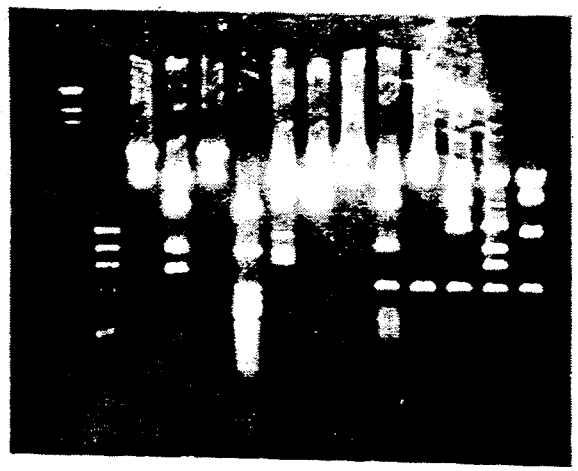

One clone was restriction mapped first by digestion with BamH1, HindIII, MspI, PstI, and SalI. The results are shown in FIG. 1A: MspI, lambda/HindIII, phageΦX174, uncut DNA, BamHI, BamHl, BglII, BstEII, ClaI, NcoI, SnaB1, StuI and XhoI was also performed on the clone. The double digestion mixture contained 24 microliters TE, 1 microliter DNA, 3 microliters restriction enzyme-buffer, 1 microliter EcoRl, and 1 microliter of the second restriction enzyme. The mixture was reacted 1.25 h at 37° C. Controls of the EcoR1 digested DNA, uncut DNA, and lambdaHindIII+phageΦX174 were also run. The results of he double digestion are shown in FIG. 1B: lambda marker, phageXΦX174, uncut plasmid, EcoR1, R1+BamHI, R1+BstEII, R1+ClaI, R1+NcoI, R1+SnaBI, R1+StuI, R1+XhoI. The results of a triple digestion are shown in FIG. 1C: lambda, phageΦX174, EcoR1, EcoR1-+BamHI, EcoR1+HindIII, EcoR1+MspI, EcoR1+-NcoI, EcoR1+PstI, EcoR1+SalI, EcoR1BglII+-BamHI, EcoR1+lII+HindIII, EcoR1+BlII+PstI, EcoR1+lII+StuI, EcoR1+lII+XhoI.

The sex-specific DNA has also been cloned in phage M13.

EXAMPLE OF THE USE OF THE SEX-SPECIFIC PIG PROBE FOR SCREENING

Figure 2:
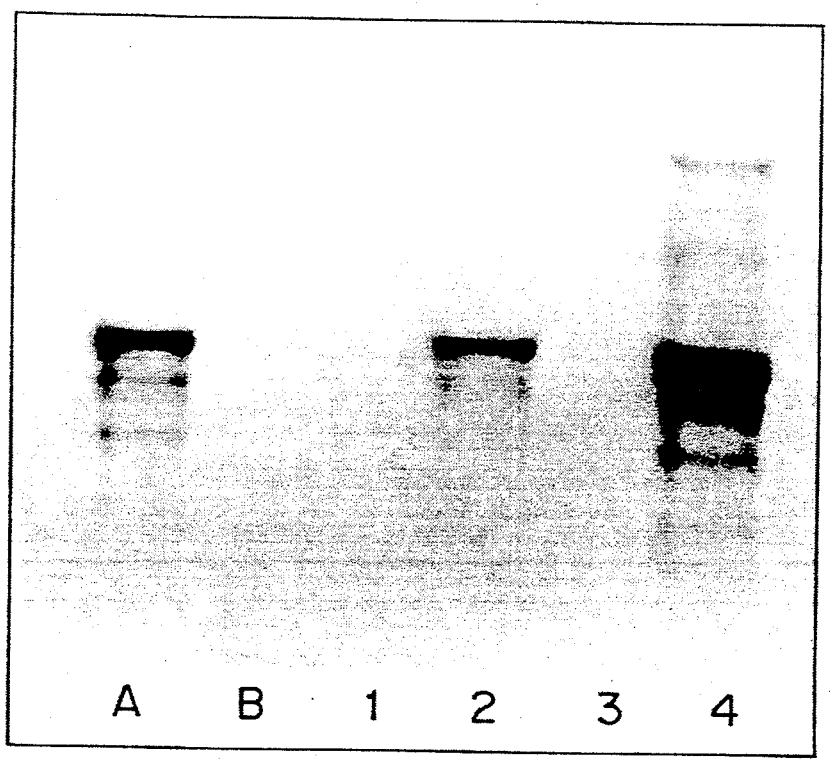
FIG. 2 is a Southern blot demonstrating the sex-specificity of the pig DNA sequence when hybridized with DNA from male and female pigs.

The insert fragment was isolated from an electrophoresed gel, labelled, and shown to hybridize specifically with male pig DNA both in dot blots and in Southern blots. Prolonged exposure of the Southern blots indicated that sequences hybridizing to the cloned probe were present in female DNA, but at a very much reduced level (less than 300-fold). The gel after 2.25 h is shown in FIG. 2: from left to right is DNA from a male, a female, a female, a male, a female, and a male pig. The specificity of the probe is striking.

CHICKEN

EXAMPLE OF THE PREPARATION OF A SEX-SPECIFIC CHICKEN PROBE

Chicken blood was prepared in the same manner as the pig blood to isolate the DNA using XhoI for the initial digestion. Two prominant bands, one of approximately 600 bases and the other of 1200 bases, appear to be present in the female chicken DNA which are not present in the male chicken DNA. The DNA from both bands was eluted from the gel and cloned at the SalI site in both M13 phage and pUC9 which was then inserted into *E. coli* (the phage into strain DH5α, the plasmid into strain JM83). Other hosts and vectors are available and can be used. Although the methods are very similar for isolating and characterizing the DNA sequences from chicken to those used with the pig DNA, SalI is used instead of EcoRI to linearize the DNA.

Subsequent analysis of the cloned DNA indicated that the DNA in both bands is very similar with the exception of the internal XhoI site. Both contain smaller imperfectly repeating units. Probes prepared from the approximately 600 base DNA will hybridize to the approximately 1200 base DNA. A clone of the 600 base DNA in the XhoI site of pUC9 was deposited With the ATCC on Jan. 21, 1988 and assigned ATCC 40418.

Figure 3:
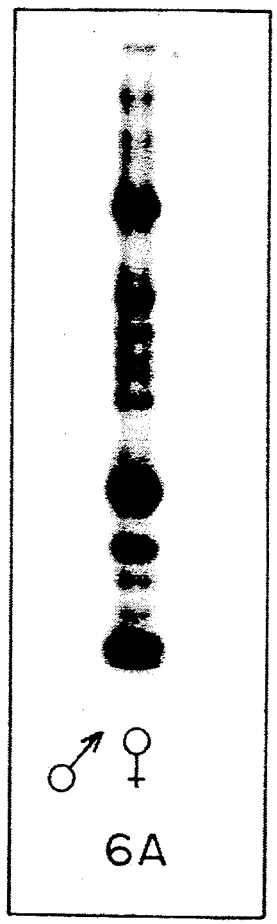
FIG. 3 is a Southern blot demonstrating the sex-specificity of the chicken DNA sequence when hybridized with DNA from male and female chickens.

The specificity of the cloned DNA for female chicken DNA is demonstrated by the autoradiogram of a Southern blot comparing hybridization with male and female chicken DNA, shown in FIG. 3. Male chicken DNA is on the left, female chicken DNA is on the right. There is no apparent hybridization of the cloned DNA with the male chicken DNA.

The present invention has significant advantages over the methods presently available to predict the sex of livestock. Essentially any improvements in the ability of livestock producers to control the sex of offspring is beneficial. The monetary value of a successful sex ratio control in cattle has been estimated at 50 million dollars at the national level. It is equally probable that the swine and poultry industry would also benefit enormously from methods to predetermine sex. Further, the methods and probes Will provide useful basic information concerning the structure and function of sex-specific DNA in livestock animals.

Modifications and variations of the present invention, sex-specific nucleotide sequences for livestock species including the pig and chicken will be obvious to those skilled in the art from the foregoing detailed description. Such modifications and variations are intended to come within the scope of the appended claims.

We claim:

1. An isolated repetitive nucleic acid fragment present in the DNA isolated from the somatic cells of male pigs wherein said fragment is present in reduced levels in the DNA isolated from the somatic cells of female pigs and further wherein said fragment is the insert portion of the pUC8 plasmid clone deposited with the American Type Culture Collection on Jan. 21, 1988 and assigned ATCC number 40417.

2. The fragment of claim 1 labelled for use as a probe.

3. The fragment of claim 1 incorporated into a vector.

4. The fragment of claim 3 ligated into pUC8 and deposited with the American Type Culture Collection, Rockville, Md. on Jan. 21, 1988 and assigned ATCC number 40417.

5. A method for characterizing DNA which determines the sex of a pig comprising providing an isolated repetitive nucleic acid fragment present in the DNA isolated form the somatic cells of male pigs wherein said fragment is present in reduced levels in the DNA isolated from the somatic cells of female pigs and further wherein said fragment is the insert portion of the pUC8 plasmid clone deposited with the American Type Culture Collection on Jan. 21, 1988 and assigned ATCC number 40417, and contacting the repetitive nucleic acid fragment with a sample containing DNA from an animal whose sex is to be determined.

6. The method of claim 5 further comprising labelling the nucleic acid fragment and hybridizing the labelled fragment with DNA from the source of DNA to be characterized.

7. The method of claim 6 comprising hybridizing the labelled fragment with DNA from pig sperm.

8. The method of claim 6 comprising hybridizing the labelled fragment with DNA from a pig embryo.

* * * * *